(12) United States Patent
Kelley et al.

(10) Patent No.: US 11,497,391 B2
(45) Date of Patent: Nov. 15, 2022

(54) JOINTED SPECULUM

(71) Applicant: Timothy F. Kelley, MD Inc., Newport Beach, CA (US)

(72) Inventors: Timothy K Kelley, Newport Beach, CA (US); Clayton Heiser, Newport Beach, CA (US)

(73) Assignee: TIMOTHY F. KELLEY, MD INC., Newport Beach, CA (US)

( * ) Notice: Subject to any disclaimer, the term of this patent is extended or adjusted under 35 U.S.C. 154(b) by 0 days.

(21) Appl. No.: 16/910,233

(22) Filed: Jun. 24, 2020

(65) Prior Publication Data
US 2021/0401280 A1 Dec. 30, 2021

(51) Int. Cl.
*A61B 1/227* (2006.01)
*A61B 1/233* (2006.01)
*A61B 1/32* (2006.01)
*A61B 1/06* (2006.01)

(52) U.S. Cl.
CPC ............ *A61B 1/227* (2013.01); *A61B 1/0661* (2013.01); *A61B 1/233* (2013.01); *A61B 1/32* (2013.01)

(58) Field of Classification Search
CPC ........... A61B 1/227; A61B 1/233; A61B 1/32; A61B 1/0661; A61B 1/2275
USPC ........ 600/190, 193, 197, 200, 206, 210, 220
See application file for complete search history.

(56) References Cited

U.S. PATENT DOCUMENTS

| 220,762 | A | * | 10/1879 | Huffman | A61B 1/32 600/223 |
|---|---|---|---|---|---|
| 325,647 | A | * | 9/1885 | Baily | A61B 1/32 600/222 |
| 400,589 | A | * | 4/1889 | Molesworth | A61B 1/32 600/203 |
| 10,765,309 | B1 | * | 9/2020 | Alsaifi | A61B 1/00089 |
| 2002/0019583 | A1 | * | 2/2002 | Elliott | A61B 1/00087 600/200 |
| 2004/0184288 | A1 | * | 9/2004 | Bettis | A61B 1/303 362/572 |
| 2008/0123717 | A1 | * | 5/2008 | Lane | A61B 1/227 374/209 |

FOREIGN PATENT DOCUMENTS

WO WO-0071017 A1 * 11/2000 ............. A61B 1/227

* cited by examiner

*Primary Examiner* — Eduardo C Robert
*Assistant Examiner* — David C Comstock
(74) *Attorney, Agent, or Firm* — Irving Keschner

(57) ABSTRACT

A speculum having an elongated portion with two hinged jaws. In a first mode, the jaws are positioned adjacent each other and in a second mode, the jaws are spaced apart. The speculum is designed such that another identical speculum can be stacked on the original speculum.

7 Claims, 10 Drawing Sheets

JOINTED SPECULUM

BACKGROUND OF INVENTION

1. Field of the Invention

The present invention relates to a speculum for accessing and examining an internal chamber of a human body, such as the external ear canal and nasal vestibule.

2. Background of the Invention

Speculums of various types have been long available in the prior art. For example, many speculums are solid and have a fixed view as shown in U.S. Pat. No. 8,211,013.

What is desired to provide a speculum that improves access to the body cavities thus allowing for improved diagnose and treatment of body cavities through enlarged access at the critical entry point.

SUMMARY OF THE PRESENT INVENTION

The present invention provides a novel speculum that provides significant improvements over the prior art speculums. Specifically, the speculum of the present invention includes a base portion and an elongated portion extending from the rear surface of the base portion. The elongated portion comprises a pair of hinged jaws. A trigger device has one leg attached to the external surface of one jaw, the other leg being positioned adjacent a notch formed in the rear of the base portion. After the elongated portion is inserted into the body cavity to be examined, the user presses the curved portion portion of the trigger into the notch which, in turn causes the jaw attached to the trigger to rotate to an open position enabling the jaw to engage the inner tissues of the body chamber and open that portion of the body for better viewing and/or for manipulation. The speculum is designed so that an identical speculum can be stacked thereon.

The present invention thus provides a simplified speculum that allows a better view of the body cavity being examined by actively opening the body cavity. It also enables multiple speculums to be stacked on top of the other to minimize the storage area required for medical supplies.

DESCRIPTION OF THE DRAWINGS

For a better understanding of the present invention as well as other objects and further features thereof, references are made to the following description which is to be read in conjunction with the accompanying drawing wherein.

DESCRIPTION OF THE INVENTION

Figure 1:
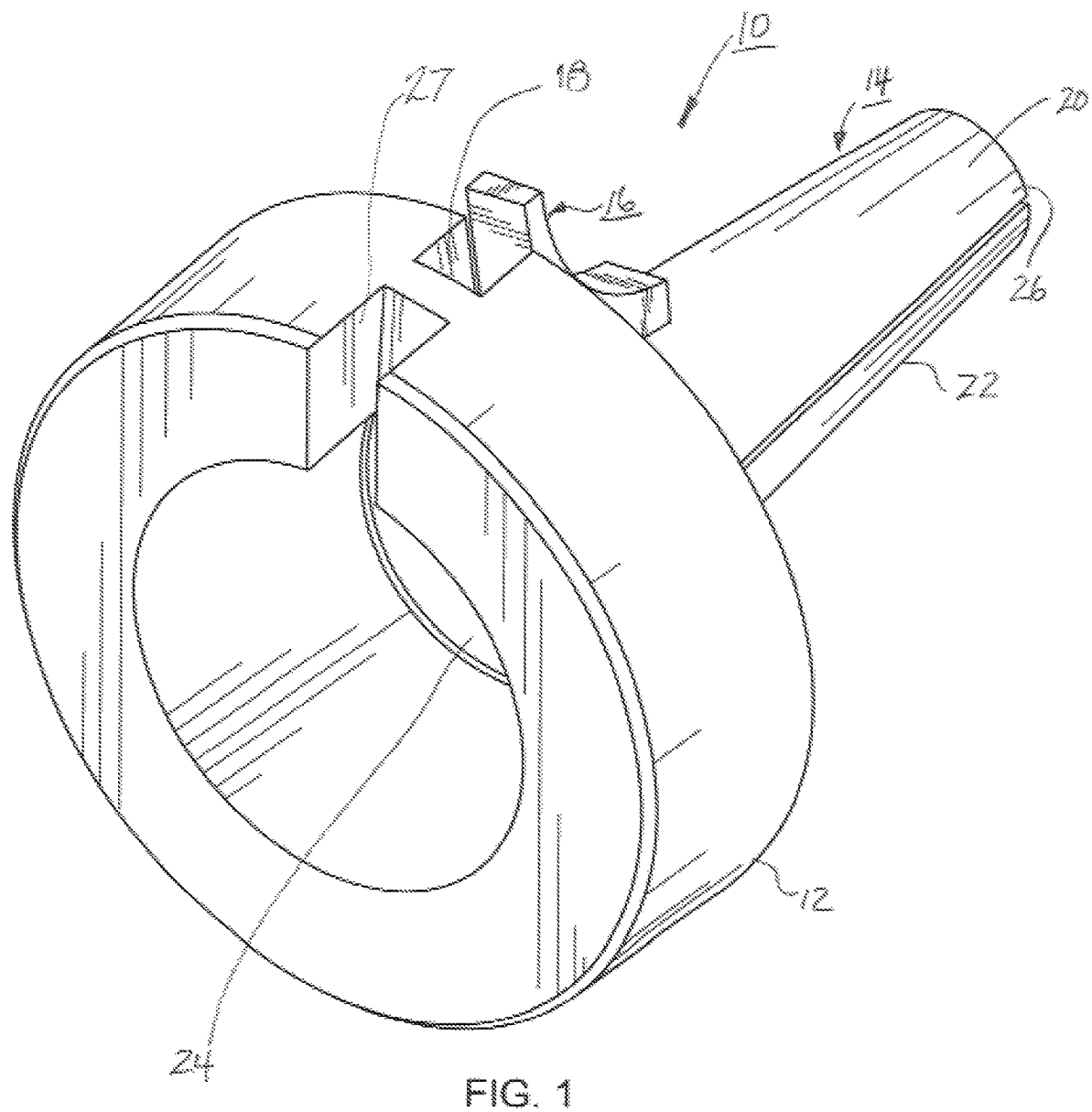
FIG. 1 is a rear, bottom, three quarter perspective view of the speculum of the present invention with the jaws in the closed position.
Figure 10:
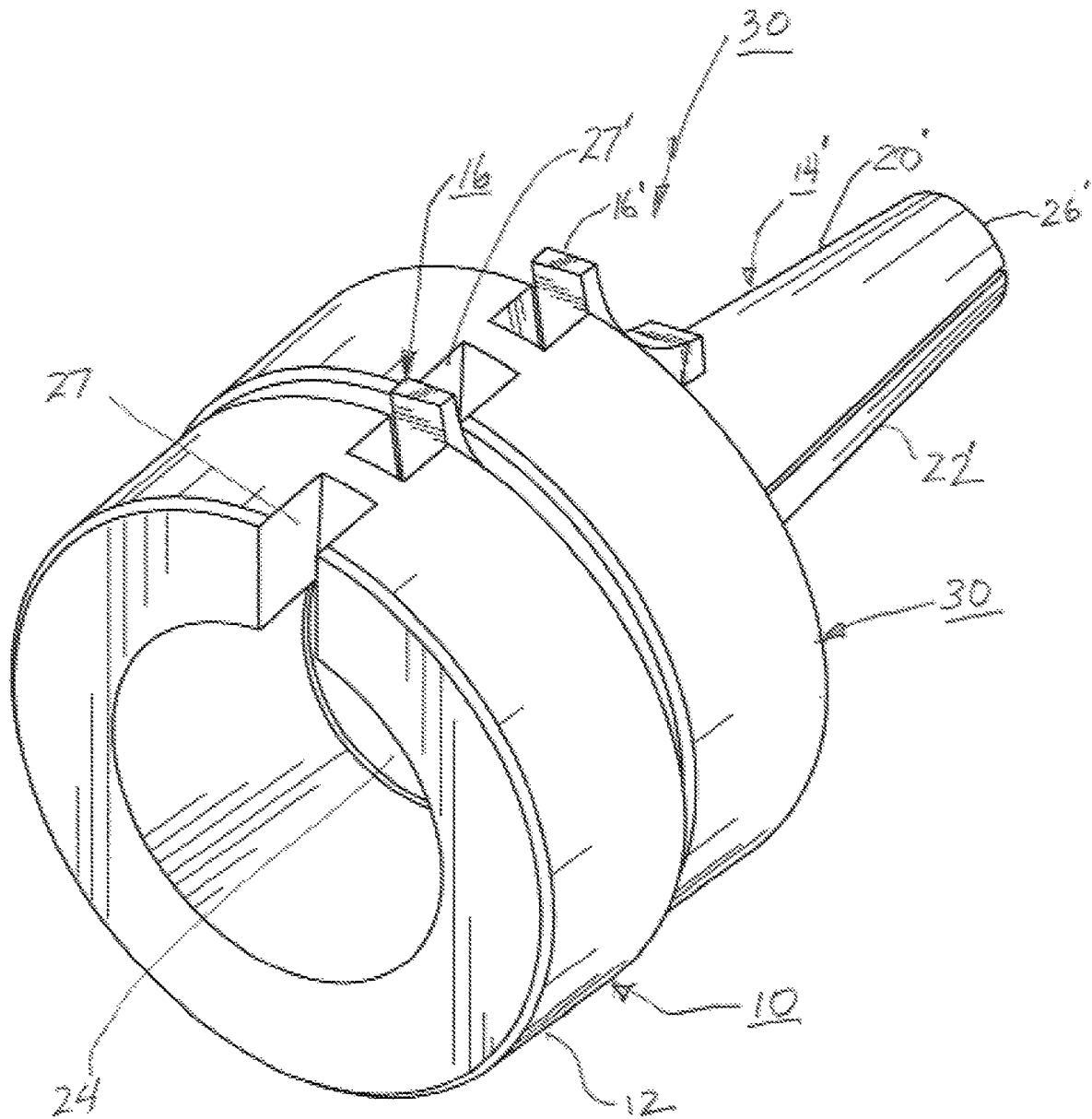
FIG. 10 illustrates two speculums of the present invention stacked together.

Referring to FIG. 1, a rear perspective view of the jointed speculum 10 of the present invention is illustrated. Speculum 10 is comprised of a base section 12, an elongated cone shaped portion 14, tab trigger 16 and a notch 18. Circumferential edge 21 (FIG. 2) of portion 14 is spaced-apart from the rear surface 25 of base portion 12 by active hinge 13. Active hinge 13 has one end 15 attached to the rear surface 25 of base portion 12. Portion 14 is split into two halves forming jaw portions 20 and 22. The hinge function of 13 is "activated" when backward pressure is applied to trigger tab 16, causing separation of jaw portions 20 from portion 22. A stacking notch 27 formed in section 12 enables the stacking speculums to be stacked one on top of the other as illustrated in FIG. 10.

Base section 12 is typically joined to a light source (not shown) and has a viewing window 24. In essence, there are two main otoscope attachment methods, the first wherein speculum 10 slides over a cone and then rotated such that it locks into a notch formed in the octoscope. The second method is to slide speculum 10 inside a cylindrical member, speculum 10 being secured to the member by friction fitting. The girth of base section 12 allowing speculum 10 to be a universal fit to both attachment methods thus avoiding the necessity of producing different sized bases for different products. The tip 26 of portion 14 narrows to a circular or oval shape which is small enough to insert into the body chamber being examined, such as the external ear canal or nasal vestibule of a patient. Trigger 16 is engaged by the finger (of the doctor) doing the examination and with activation, enables jaw portions 20 and 22 to be separated, jaw portion 20 then engaging tissues along the inside of the body chamber selected for examination forcing open its walls. This enables the examiner a much wider view of the body chamber than is possible with a fixed view provided by standard, prior art solid speculums. This movement opens the mouth of the body chamber, thereby temporarily enlarging and stretching it open to allow for removal of a foreign body or insertion of some type of treatment device, instrument or medication, etc.

Trigger 16 is always under pressure from the examiner's finger until it friction fits within notch 18 at the point where it is at its maximum spaced-apart position. Before latching, the examiner keeps pressure on the notch enabling the jaw portions 20 and 22 to be gradually opened and enabling the examiner to explore and move around the body cavity being examined.

The jointed speculum 10 preferably comprises molded plastic. The stacking notch 27 enables a number of speculums 10 to be joined together as shown in FIG. 10 to minimize storage requirements and enable easy access to a speculum positioned below a speculum that has been removed for use, the used speculum being easily disposed of. Speculum 10 is easily adapted for used with existing tools and devices.

Figure 2:
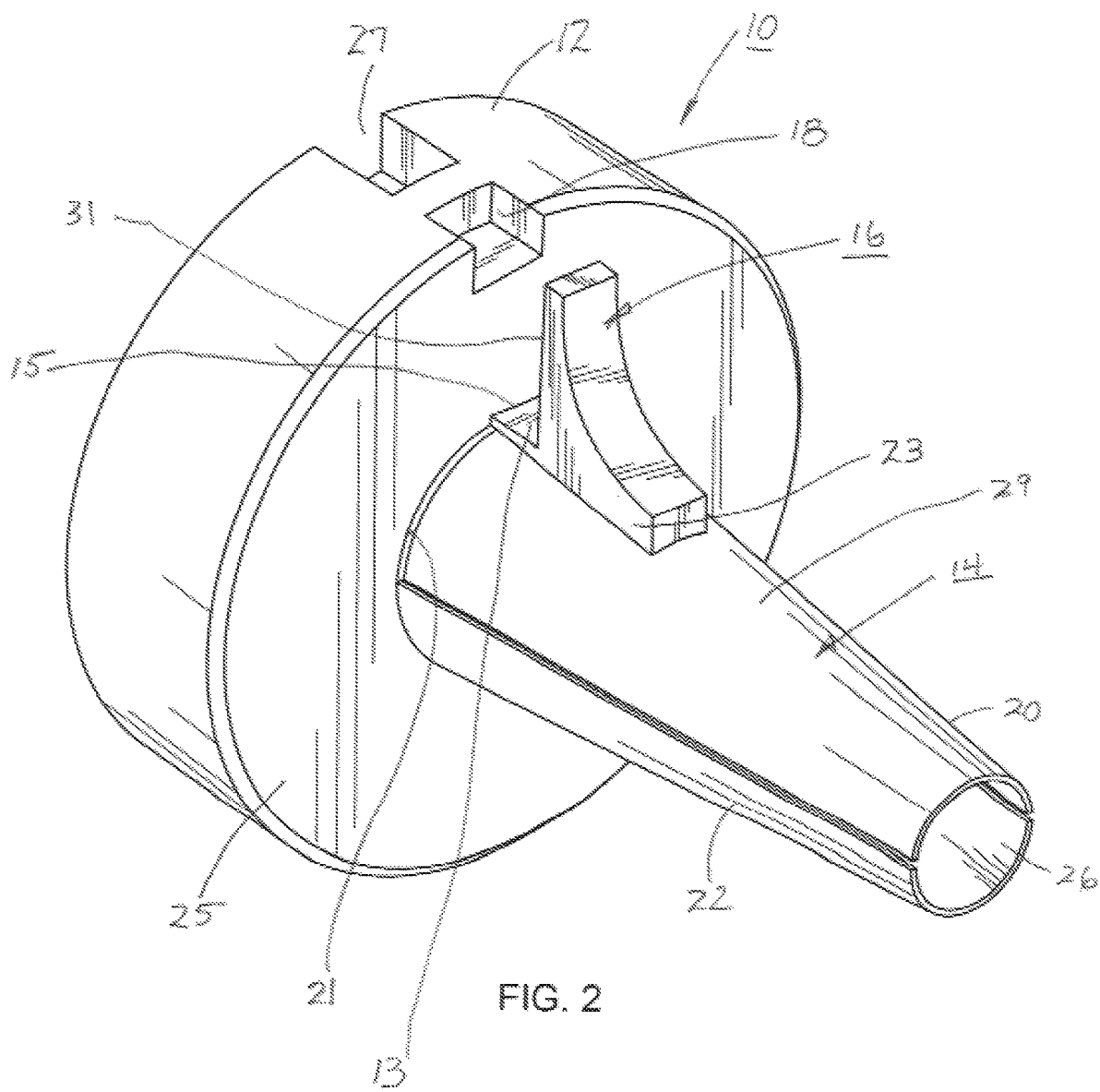
FIG. 2 is a front, bottom, three quarter perspective view of the speculum of the present invention.

FIG. 2 is a front perspective view of the speculum 10 shown in FIG. 1. This figure clearly shows trigger mechanism 16 with legs 23 and 31, leg 23 being secured to the exterior surface 29 of elongated portion 14. Jaw portions 20 and 22 are hinged via extension, or post member, 13 which functions as an active hinge member. When a user presses trigger 16 backwards after speculum 10 is inserted into the body cavity being examined, portion 16 is gradually forced into notch 18 and, at the same time, jaw 20 is pulled "opened" upwardly to the position shown in FIG. 9, the maximum spaced-art position.

Figure 3:
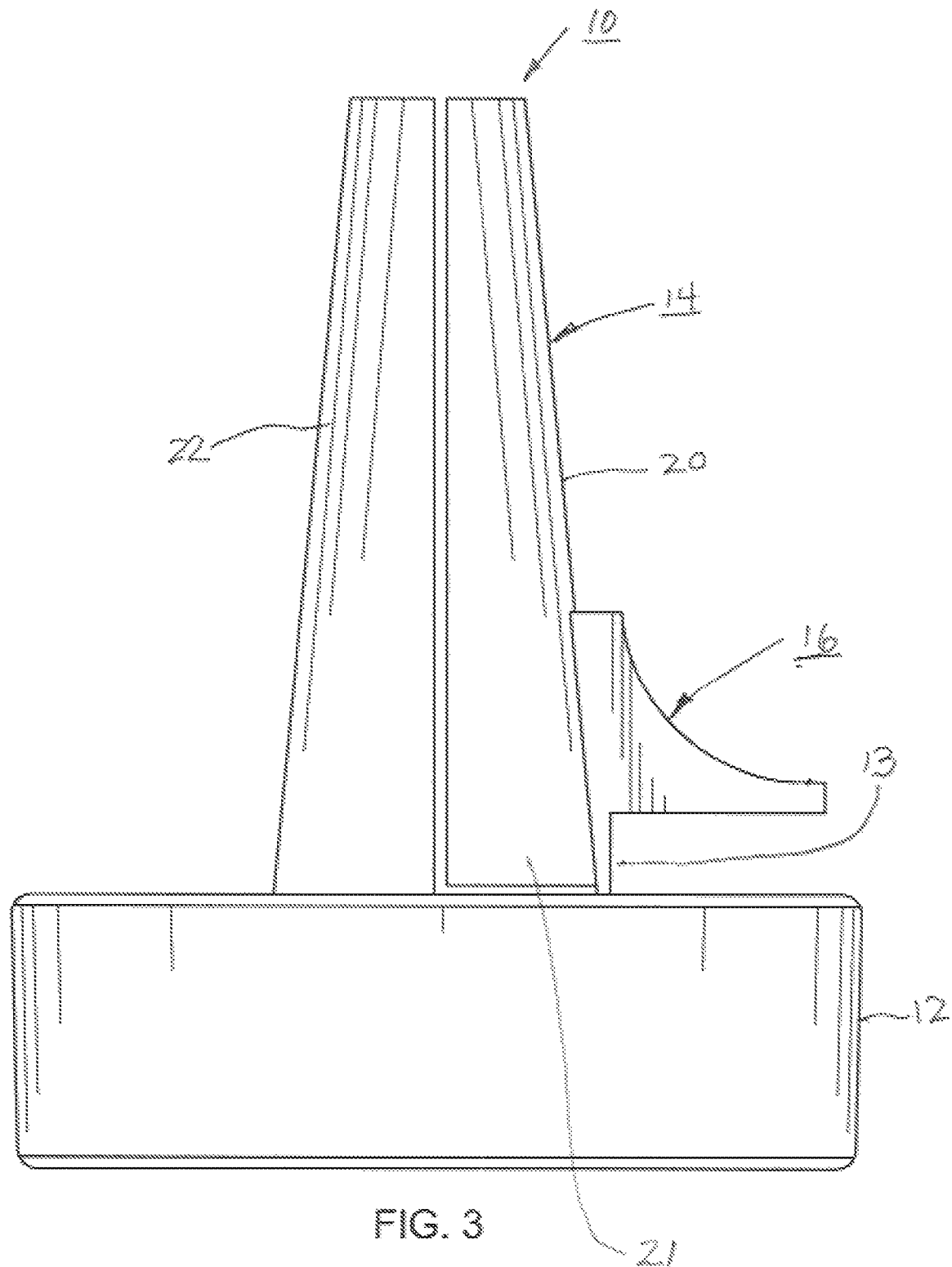
FIG. 3 is a right side view of the speculum of the present invention.
Figure 4:
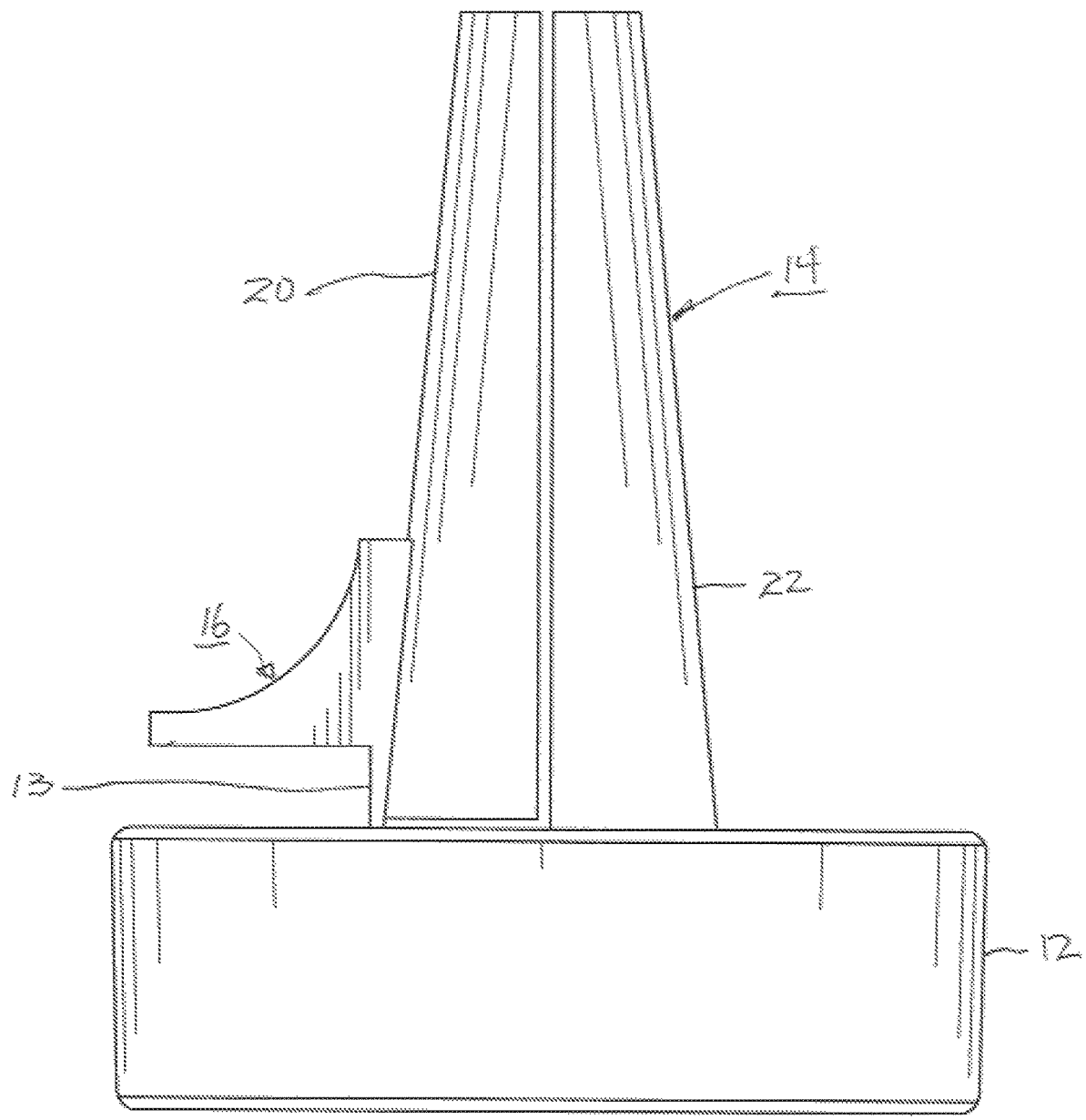
FIG. 4 is a left side view of the speculum of the present invention.
Figure 5:
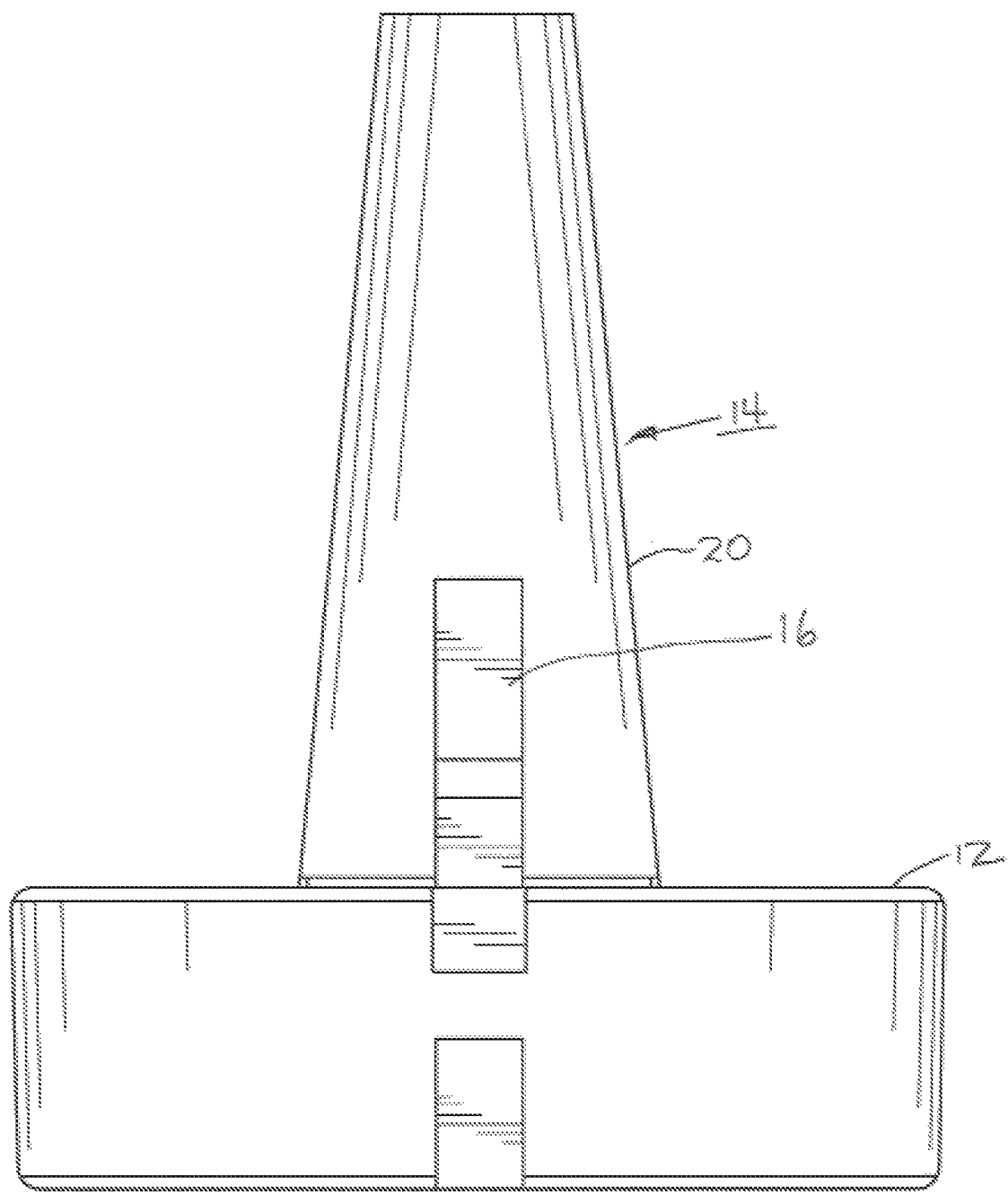
FIG. 5 is a bottom view of the speculum of the present invention.
Figure 6:
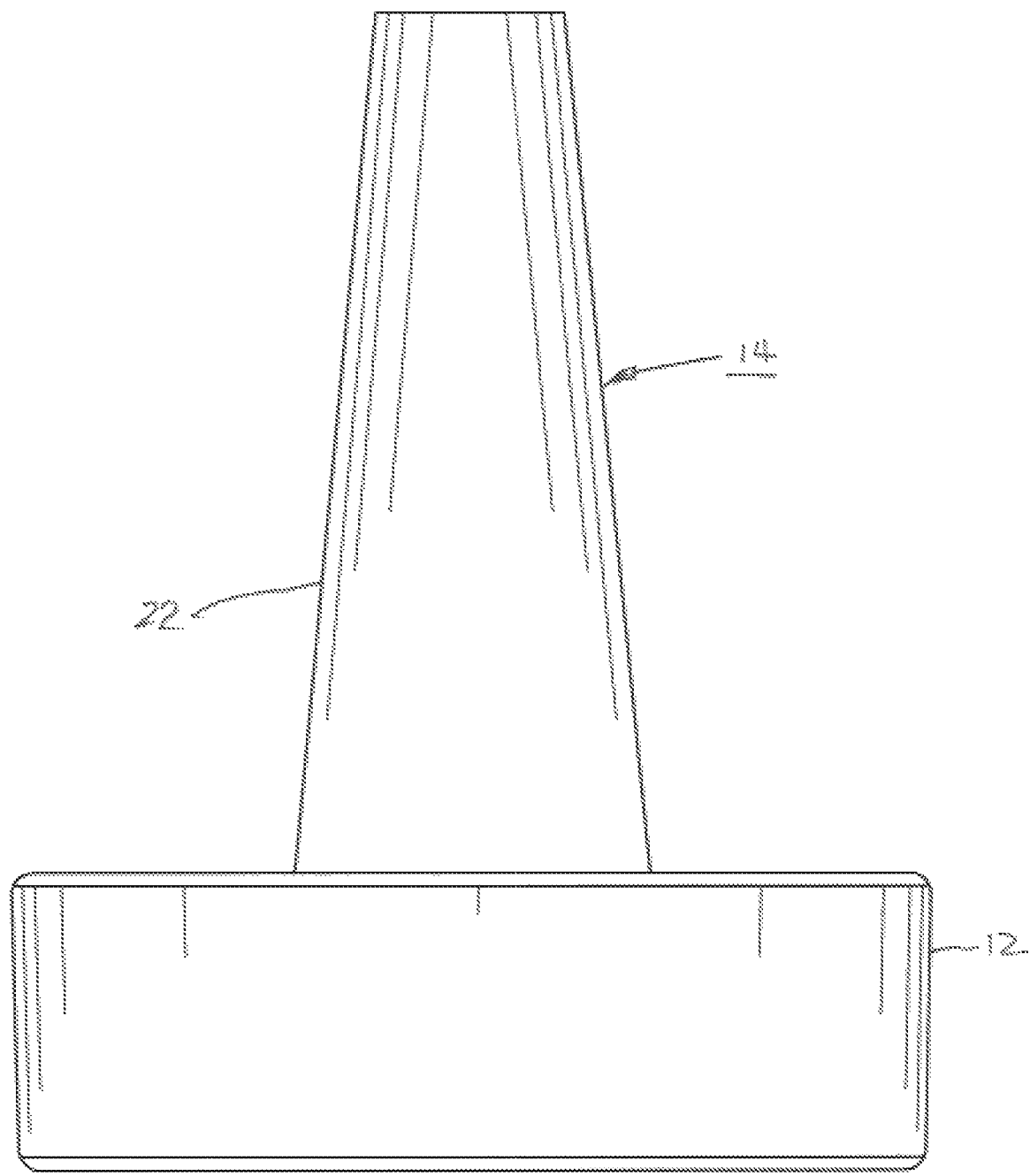
FIG. 6 is a top view of the speculum of the present invention.
Figure 7:
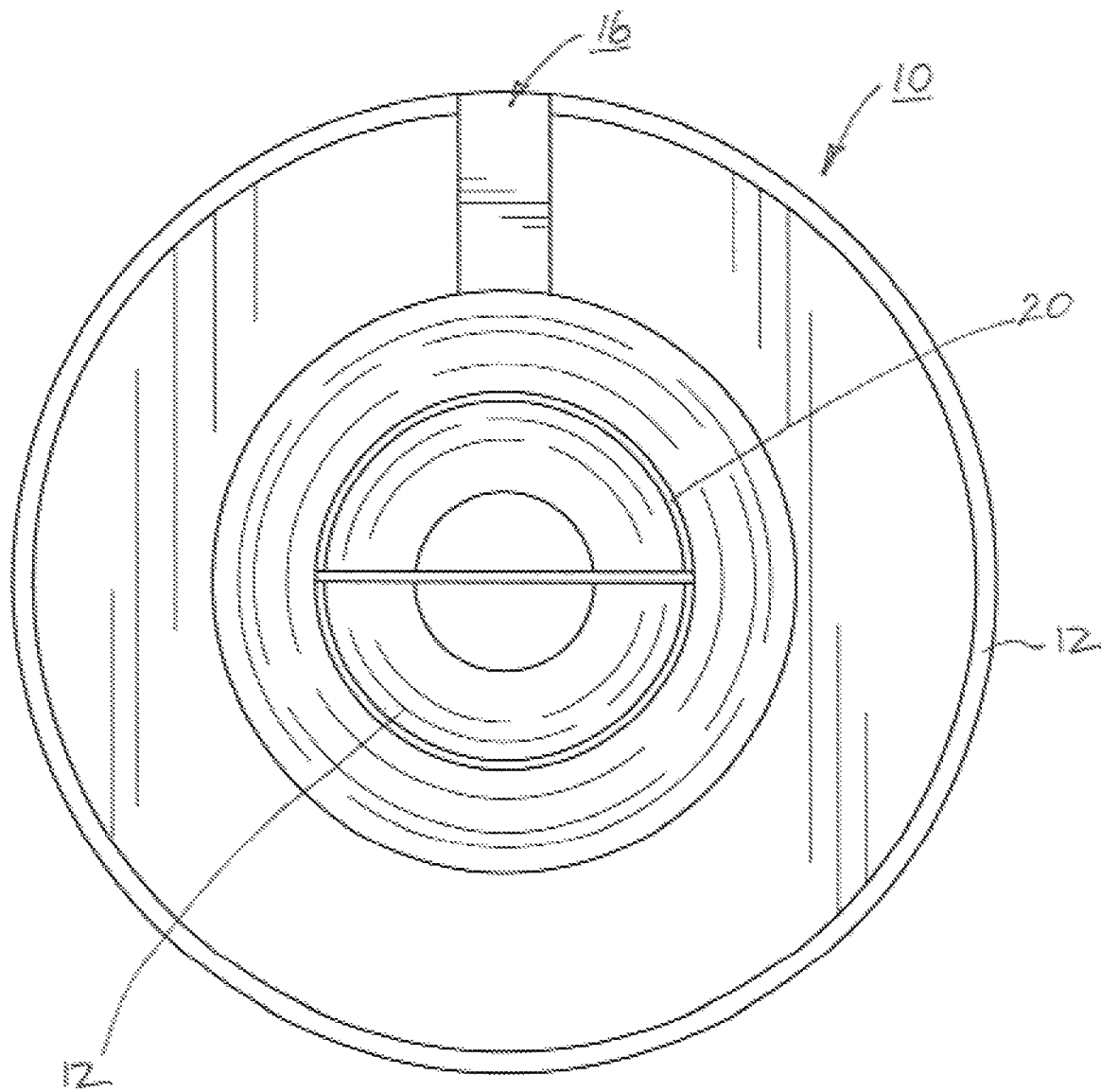
FIG. 7 is a bottom up front view, top side down perspective view of the speculum of the present invention.
Figure 8:
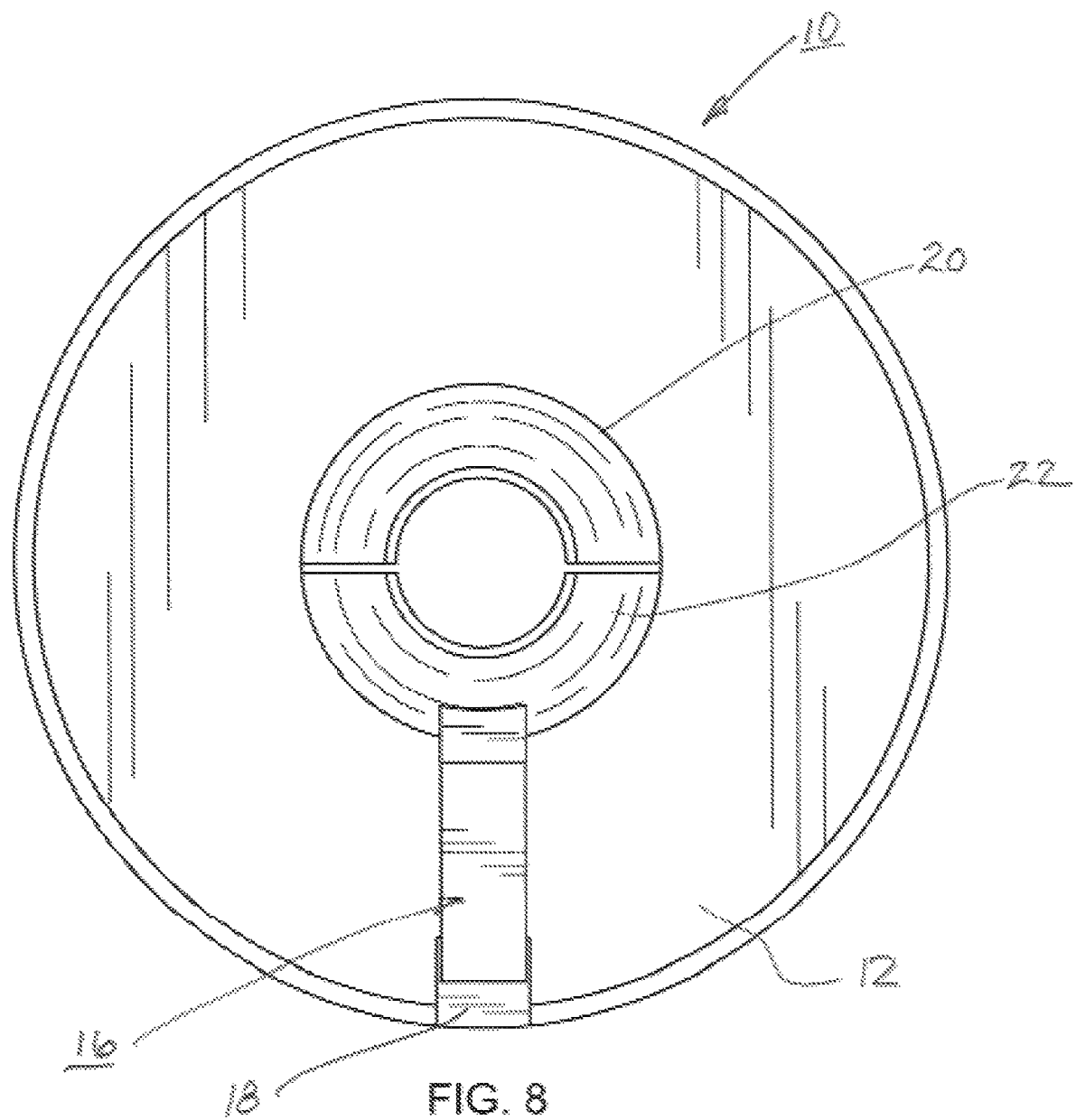
FIG. 8 is a bottom down front view, top side up perspective view of the speculum of the present invention.
Figure 9:
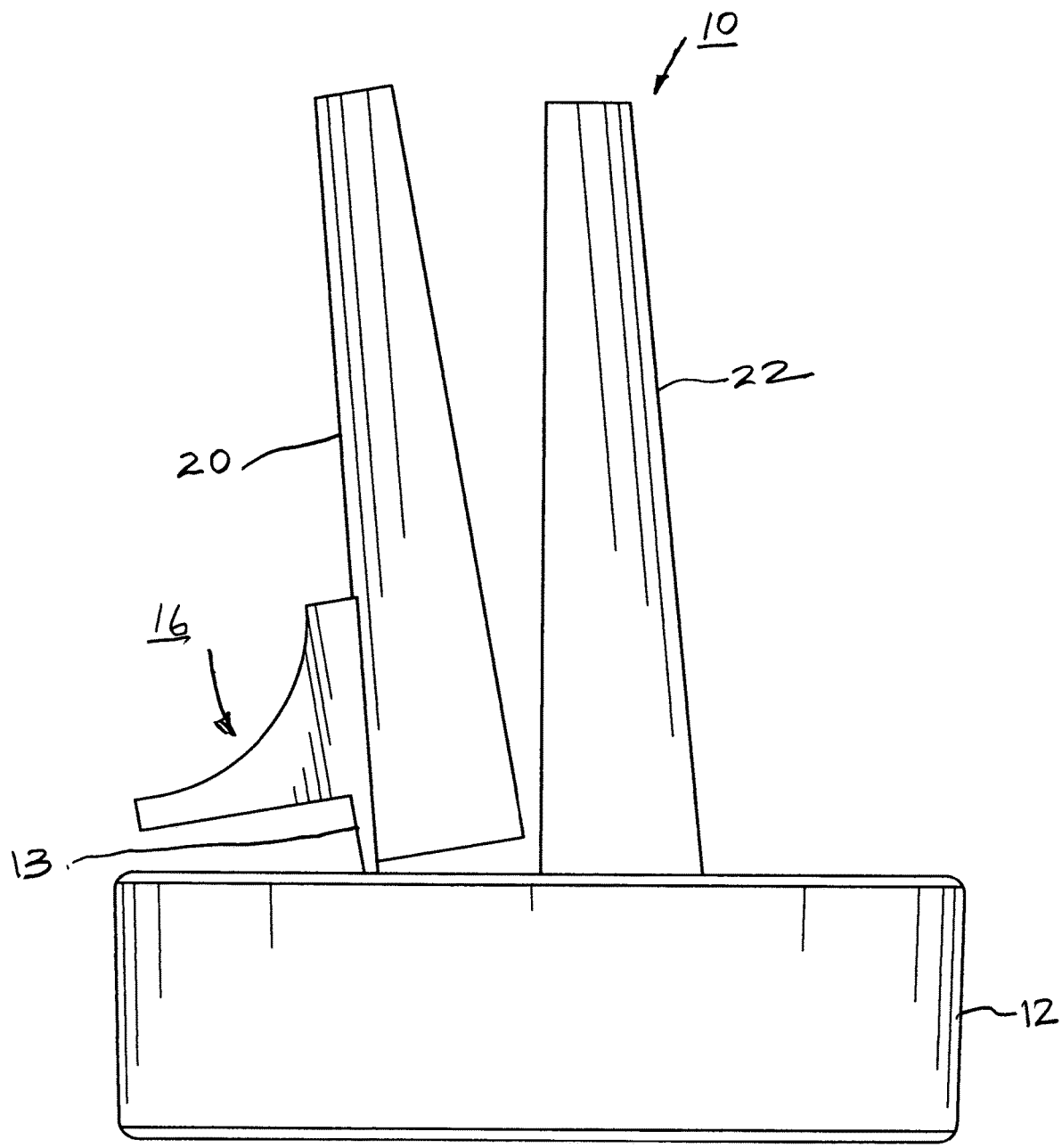
FIG. 9 is a front perspective view of the speculum of the present invention with the jaws in the open position.

FIG. 3 is a right side view of the speculum 10 of the present invention, FIG. 4 is a left side view of speculum 10, FIG. 5 is a bottom view of speculum 10, FIG. 6 is a top view of speculum 10, FIG. 7 is a bottom up front view of speculum 10, FIG. 8 is a bottom down front view of speculum 10, FIG. 9 illustrates speculum 10 with the jaws spaced apart in the "open" position and FIG. 10 illustrates a second speculum 30 stacked onto original speculum 10, notch 27' of speculum 30 engaging trigger 16 of speculum 10 (reference numerals 14'0.16'. 20', 22' and 26' identify corresponding identical components shown and identified in FIGS. 1-9).

While the invention has been described with reference to its preferred embodiments, it will be understood by those skilled in the art that various changes may be made and equivalents may be substituted for elements thereof without departing from the true spirit and scope of the invention. In addition, many modifications may be made to adapt a particular situation or material to the teachings of the invention without departing from its essential teachings.

What is claimed is:

1. A first speculum apparatus with a base portion having front and rear surfaces and an elongated portion wherein first and second jaw portions are attached thereto comprising:
   a device having first and second leg members, said first leg member being in contact with the external surface of said elongated portion;
   a first notch formed in said rear surface of said base portion, said second leg member being positioned adjacent said first notch; and
   a second substantially identical speculum stacked on top of said first speculum said second speculum engaging a second notch formed in the front surface of said base portion to enable stacking of said first and second speculums.

2. The speculum apparatus of claim 1 wherein the device is configured such that a user of said first speculum presses said leg member in said first notch thus moving said second leg member of said device away from the external surface of said elongated portion whereby said first and second jaw portions are spaced apart.

3. The speculum apparatus of claim 2 further including an active hinge member attached to said device, the active hinge member acting as a pivot to enable said first jaw portion to separate from said second jaw portion.

4. The speculum apparatus of claim 1, wherein said first speculum includes an area for receiving an external light source.

5. The speculum apparatus of claim 1 further including a third identical speculum stacked on top of said second speculum, said third speculum engaging the second notch formed in the front surface of said base portion on said second speculum.

6. The speculum of claim 1 further including a viewing window positioned in the base portion of said first speculum to enable a user to view a body chamber being examined.

7. The speculum of claim 1 wherein said first, speculum is fabricated from molded plastic.

* * * * *